United States Patent [19]

Bridges

[11] Patent Number: 4,962,194
[45] Date of Patent: Oct. 9, 1990

[54] METHOD OF PREPARING 51,N6-DISUBSTITUTED ADENOSINES FROM INOSINES

[75] Inventor: Alexander J. Bridges, Ann Arbor, Mich.

[73] Assignee: Warner-Lambert Company, Morris Plains, N.J.

[21] Appl. No.: 260,202

[22] Filed: Oct. 19, 1988

Related U.S. Application Data

[63] Continuation of Ser. No. 34,125, Apr. 2, 1987, abandoned.

[51] Int. Cl.$^5$ .................... C07H 19/167; C07H 19/20
[52] U.S. Cl. ........................ 536/26; 536/23; 536/24; 536/27; 536/28
[58] Field of Search ............................ 536/23, 24, 26

[56] References Cited

U.S. PATENT DOCUMENTS 3,282,921  11/1966  Verheyden et al. ............... 536/23
4,373,097  2/1983  Stramentinoli et al. ............. 536/26

OTHER PUBLICATIONS

Feiser & Fieser, Reagents for Organic Synthesis, vol. 1, John Wiley & Sons, Inc., New York, N.Y., 1967, see pp. 1247–1249.

Fieser & Fieser, Reagents for Organic Synthesis, vol. 6, John Wiley & Sons, Inc., New York, NY, 1977, see pp. 645–648.

Acheson, An Introduction to the Chemistry of Heterocyclic Compounds, Wiley-Interscience, New York, NY, 1967, pp. 211, 212, 338, 339.

Goodman (I), "Chemical Synthesis and Transformations of Nucleosides", in Basic Principles of Nucleic Acid Chemistry by Ts'O, Academic Press, New York, NY, 1974, pp. 151, 154, 155 & 159.

Goodman (II), "Chemical Synthesis and Transformations of Nucleosides", in Basic Principles of Nucleic Acid Chemistry by Ts'O, Academic Press, New York, NY 1974, see pp. 136–138.

*Primary Examiner*—John W. Rollins
*Assistant Examiner*—L. Eric Crane
*Attorney, Agent, or Firm*—Joan Thierstein

[57] ABSTRACT

A processing for preparing 5'-N,6-disubstituted adenosines from inosines. The adenosines have usefulness as neuroleptics, analgesics, cardiotonics, antihypertensives, antilipolytics, antihyperlipaemics, antiinflammatory agents, antithrombotic or antiembolic agents.

5 Claims, No Drawings

METHOD OF PREPARING 51,N6-DISUBSTITUTED ADENOSINES FROM INOSINES

This is a continuation of U.S. Application Ser. No. 034,125, filed Apr. 2, 1987 now abandoned.

BACKGROUND OF THE INVENTION

The present invention is useful for preparing 5'-N6-disubstituted adenosines having variously neuroleptic, analgesic, antilipolytic, antihyperlipaemic, antiinflammatory, antithrombotic, antiembolic and cardiovascular activity. More particularly, the process of the present invention is for the preparation of intermediates useful in the preparation of a wide variety of the 5'-modified adenosines in high yields. Further, contrary to previously known processes the process provides a single step for the preparation of the intermediates from, for example, inosine isopropylidene. Such intermediates are then treated with nucleophilic displacement agents to obtain the desired 5'-modified adenosines.

Selected processes previously known for the preparation of such 5'-modified adenosines are reviewed in U.S. Application Ser. Nos. 756,922 filed Jul. 18,1985 and 825,513, filed Jan. 31, 1986.

SUMMARY OF THE INVENTION

The present invention is a process for the preparation of a compound of the formula (I)

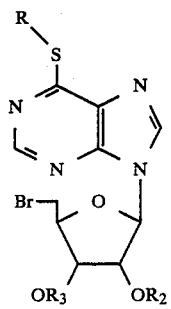

I wherein R is alkyl of from one to six carbons, aryl, heteroaryl or aralkyl, $R^2$ and $R^3$ are independently selected from the group consisting of hydrogen, alkanoyl of from one to six carbons, benzoyl, and $R^2$ and $R^3$ are taken together to form alkylidene; preferably $R^2$ and $R^3$ are taken together and are isopropylidene;

which comprises treating a compound of the formula (II)

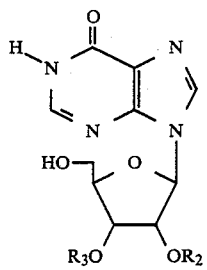

II wherein $R_2$ and $R_3$ are as defined above with the restriction $R_2, R_3 \neq H$; in a solvent with $Ar_3PBr_2$ wherein Ar is aryl or $(ArO)_3PBr_2$ wherein Ar is aryl in a solvent such as pyridine, and RSH wherein R is as defined above; to obtain the compound of formula I with an optional deprotection step to make R2 and R3 independently hydrogen.

Further, the present invention is a process for the preparation of a compound of the formula (X)

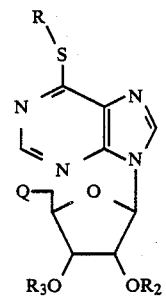

X wherein R, $R_2$ and $R_3$ are as defined above and Q is a nucleophile;

which comprises (1) treating a compound of the formula (II)

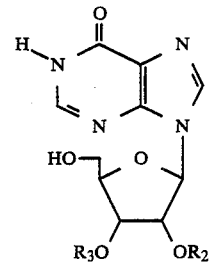

II wherein $R_2$ and $R_3$ are as defined above; with $Ar_3PBr_3$ or $(ArO)_3PBr_2$ wherein Ar is as defined above in the presence of a weak base such as pyridine; and RSH wherein R is as defined above;

and then (2) treating the product of (1) with a nucleophile;

to obtain the compound of the formula X.

It is also the present invention to provide adenosines modified at both of the N6- and 5'-positions. Therefore, the present invention is a process for the preparation of a compound of the formula (XX)

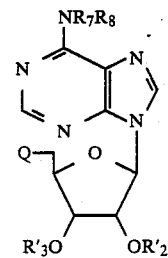

XX wherein Q is as defined above and $R'_2$ and $R'_3$ are independently hydrogen or $R_2$ and $R_3$ as defined above;

$R_7$ and $R_8$ are independently hydrogen, alkyl of from one to six carbons, cycloalkyl having a three to eleven membered ring, aryl, aralkyl, bicyclo [2.2.1.]or [2.2.2.]heptyl unsubstituted or substituted by from one to five methyl groups, 1- or 2- naphthyl, or a group selected from

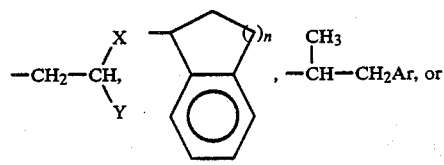 Ia

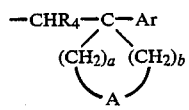

wherein X and Y are independently aryl or heteroaryl, n is one, two, or three, m is one or two, A is a bond, O, S,

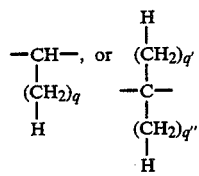

wherein q, q' or q" are independently an integer of one to four, inclusive;

a and b are independently an integer of from zero to three, inclusive, with the provision that if A is a bond then the sum of a and b must be at least two and if A is other than a bond then the sum of a and b must be at least one;

$R_4$ is hydrogen or alkyl of from one to six carbons;

with the proviso that if $R_7$ and $R_8$ are the same then both must be hydrogen or alkyl of from one to six carbons;

which comprises a process step selected from (1)
(a) treating a compound of the formula (I)

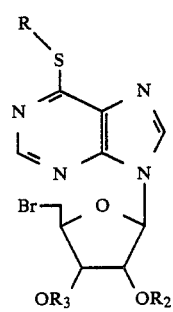 I with an oxidizing agent to obtian a compound of the formula (III)

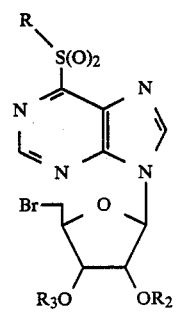 III wherein R, $R_2$, And $R_3$ are as defined above;
(b) treating the compound of formula III with a compound of the formula $HNR_7R_8$ wherein $R_7$ and $R_8$ are as defined above to obtain a compound of the formula (IV)

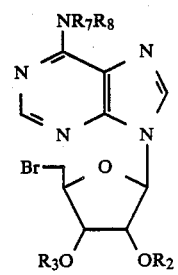 IV wherein R, $R_2$, and $R_3$ are as defined above; and then
(c) treating the compound of formula IV with a nucleophile to obtain the compound of the formula XX; and
(2) (a) treating a compound of the formula (XXX)

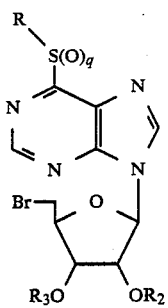 XXX wherein R, $R_2$, and $R_3$ are as defined above and q is an integer of zero or two;
with a nucleophile to obtain a compound of the formula ($X_1$)

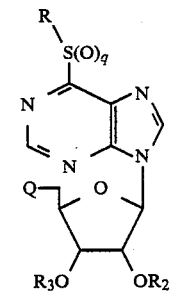 $X_1$ wherein R, q, R$_2$, R$_3$ and Q are as defined above;

and then (b) if q is zero the compound of the formula X$_1$ is treated with an oxidizing agent to obtain a compound of formula X$_1$ wherein q is two followed by treatment with a compound of the formula HNR$_7$R$_8$; and alternatively, if q is two then the compound of the formula X$_1$ is treated with a compound of the formula HNR$_7$R$_8$;

and (3) optionally hydrolyzing the products of steps 1 or 2 to obtain the compound of formula XX. The above processes are shown in the following scheme.

DETAILED DESCRIPTION OF THE INVENTION

Alkyl of from one to six carbons as used herein means a hydrocarbon chain such as methyl, ethyl, propyl, butyl, pentyl or hexyl and isomers thereof.

The term aryl as used herein means phenyl, optionally substituted by one or two of alkyl of from one to six carbons, halogen, trifluoromethyl, nitro, amino, mono- or di- alkylamino wherein alkyl is of from one to six carbons, cyano, hydroxy, alkoxy of from one to six carbons, alkylthio of from one to six carbons, and the

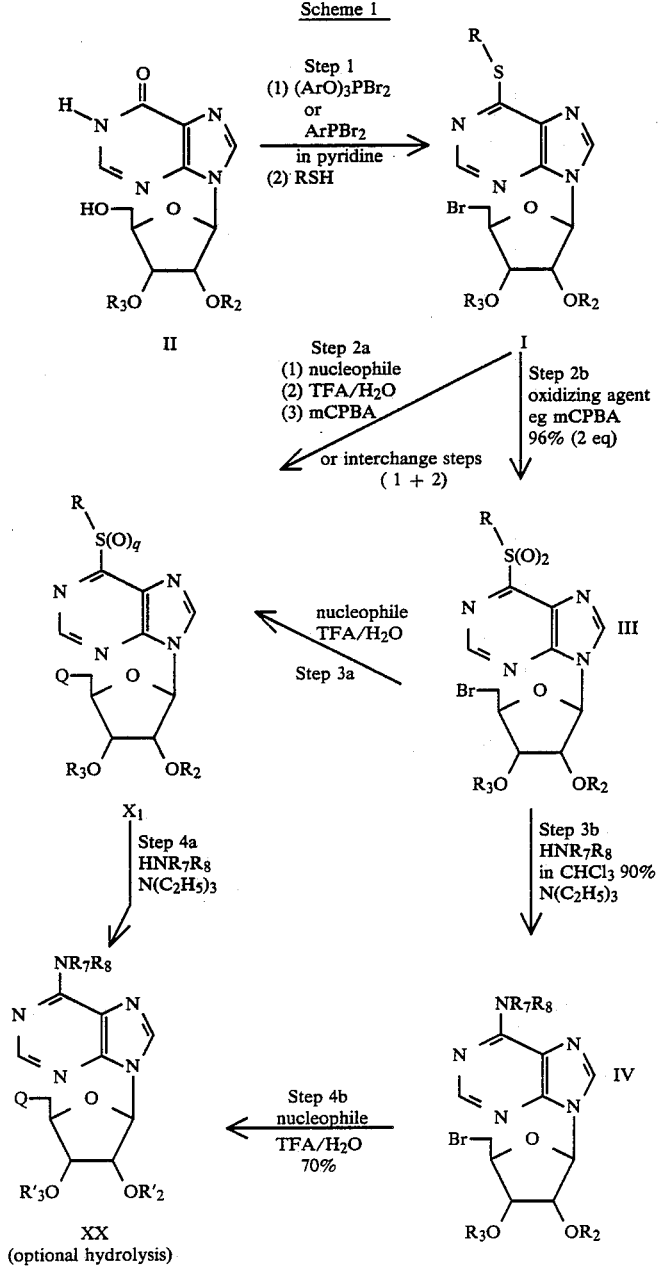

The process of step 1 as shown in Scheme 1 can be performed in a single step.

like.

The term heteroaryl as used herein means optionally substituted 2- or 3-thienyl, 2- or 3-furanyl, 2-, 4-, or 5-thiazolo, 2-, 3-, or 4-pyridyl or 2-pyrimidyl wherein the substituents are one or two of alkyl of from one to six carbons, halogen, trifluoromethyl, hydroxy, alkoxy of from one to six carbons, acyloxy of from two to six carbons, amino, mono- or di- alkylamino wherein alkyl is of from one to six carbons, alkylthio of from one to six carbons, alkylsulfonyl of from one to six carbons, or nitro.

Aralkyl as used herein is a term wherein Ar is aryl and alkyl is a hydrocarbon chain of from one to six carbons each as defined above.

Halogen is fluoro, bromo, chloro or iodo.

Nucleophile as used herein is a compound or moiety having an unshared pair of electrons. These unshared electrons are brought to the sugar moiety of the substrate which is an adenosine or its $N^6$ analog in the present invention. Particularly, the nucleophile of the present invention is hydrogen, halogen, cyano, azido, amino, lower alkoxy, lower acyloxy, lower thioalkyl, hydrazino, hydroxylamino phosphino, dialkyl or diarylcuprato.

Generally, the process of step 1 in Scheme 1 is carried out in a solvent that is a weakly basic organic medium especially pyridine. An inosine of the formula II in solvent is added to a solution of $(ArO)_3PBr_2$ or $ArPBr_2$ preferably triphenoxyphosphobromide or triphenylphosphobromide. The bromide may be prepared in situ, however, such preparation may be exothermic so the addition is with cooling to maintain the reaction between 0° and 50° C. bur preferably at about room temperature or below. Then a thiol, preferably thiophenol, is added to the reaction mixture to obtain the compound of formula I.

Compounds of formula I may be separated including purification from the reaction mixture by conventional means such as extraction, distillation, chromatography, and the like. Further, the compounds of formula I which are diastereomers having not less than five asymmetric carbons can be resolved to each stereoisomer by conventional means such as chromatography or fractional recrystallization and the like.

The steps 2a and b, 3a and b, and 4a and b are carried out by methods analogous to those known in the art.

The starting materials of the process of the present invention are readily available, are known or can be prepared by known methods.

Variations in the process of the present invention are within the skill of the art and thus the disclosure is not meant to be limiting.

EXAMPLES

5'-Deoxy-5'-bromo-S-phenylthioinosine-2',3°-di-O-isopropylidene.

Bromine (8.00 g, 50 mmol) was added dropwise to a solution of triphenyl phosphite (15.5 g, 50 mmol) in pyridine (100 mL) stirred under $N_2$ at 25° (Exotherm!). When the temperature had dropped to 25° again inosine isopropylidene (6.16 g, 20 mmol) in pyridine (100 mL) was added dropwise, with cooling. After a further five minutes thiophenol (3.30 g, 30 mmol) was added dropwise. After a further ten minutes the solvent was removed under reduced pressure at 40° . The residual intense blue-green -i slurry was dissolved in $CHCl_3$ (200 mL) and washed with water (200 mL), dilute HCl (1M, 200, 100 mL), water (100 mL), and saturated brine (100 mL) and then dried ($MgSO_4$). The solvent was removed under reduced pressure, and the residual oil was chromatographed on silica gel, eluting with ethyl acetate/hexane, to give the desired bromide (6.59 g, 71%) of solid white foam. Nmr ($CDCl_3$) δ 5 8.62, 8.16 (1H and 1H, 2s), 7.66 (2H d of d J=6, 3 Hz), 7.53–7.45 (3H, m), 6.18 (1H, d, J=2.5 Hz), 5.47 (1H, d of d J=2.5, 6.4 Hz), 5.15 (1H, d of d, J=6.4, 3.1 Hz), 4.54 (1H, d of d of d J=3.1, 7.5, 5.5 Hz), 3.61, 3.46 (1H and 1H, ABq of ds $J_{AB}$=10.5, $J_d$=7.5, 5.5 Hz), 1.63, 1.40 (3H and 3H, 2s).

5'-Deoxy-5'-bromo-S-phenylthioinosine-S,S-dioxide-2',3'-di-O-isopropylidene.

A mixture of m-chloroperoxybenzoic acid (7 g, 85%, 35 mmol) and $NaHCO_3$ (3.0 g, 35 mmol) was added in portions over five minutes to a solution of 5'-deoxy-5'-bromo-S-phenylthioinosine-2',3'-di-O-isopropylidene (6.59 g, 14 mmol) in $CHCl_3$ (100 mL) stirred under $N_2$ at 25° . After four hours the reaction mixture was diluted with $CHCl_3$ (100 mL) and was washed with water (200 mL), dilute Na solution (200 mL), and saturated brine (100 mL) and then dried ($MgSO_4$) The solvent was removed under reduced pressure to give the desired sulfone (7.54 g, 6%) containing 50 mol% $CHCl_3$ as a light yellow solid foam. Nmr ($CDCl_3$) 5 8.99, 8.55 (1H and 1H, 2s), 8.1–8.25 (2H, m), 7.4–7.6 (3H, m), 6.21 (1H,d J=2.5 Hz), 5.30, 4.98 (1H and 1H, ABq of ds JAB =6 Hz, $J_d$=2.5, 3 Hz), 4.45 (1H, d of t, Jd =3 Hz, Jt =6 Hz), 3.45, 3.36 (2H, ABq of ds, $J_{AB}$=11 Hz $J_d$=6 Hz), 1.58, 1.35 (3H and 3H, 2s).

5'-Deoxy-5'-bromo-N,6-cyclopentyladenosine-2',3'-di-O-isopropylidene triethylamine (0.81 g, 8 mmol) were added to a solution of 5'-deoxy-5'-bromo-S-phenylthioinosine-S,S-dioxide-2'3'-di-O-isopropylidene (2.15 g, =4 mmol) in $CHCl_3$ (40 mL) stirred under $N_2$ at 20°. After 14 hours the reaction mixture was washed with dilute aqueous NaH solution (0.4 M, 50 mL), water (2 x 25 mL), and saturated brine (25 mL) and then dried ($MgSO_4$). The solvent was removed under reduced pressure to give the desired adenosine (1.78 g, 89%) containing 50 mol% $CHCl_3$ as a yellow brown solid foam. Nmr ($CDCl_3$) δ 8.35, 7.84 (1H and 1H, 2s), 6.06 (1H, d, J=2.5 Hz), 5.87 (1H, br d, J=8 Hz), 5.48 (1H, d of d J=2.5, 6 Hz), 5.14 (1H, d of d J=6, 3 Hz), 4.3−4.7 (2H, m), 3.62, 3.40 (1H and 1H, ABq of ds, $J_{AB}$=10.5 Hz, $J_d$=6, 7 Hz), 1.9–2.3 (2H, m), 1.2–1.8 (12 H, m plus s at 1.63, 1.41 δ). 5'-Deoxy-5'-bromo-N,6-cyclopentyladenosine.

A 0° solution of water (1 mL) in trifluoroacetic acid (9 mL) was added to a solution of 5'-deoxy-5'-bromo-N,6-cyclopentyladenosine-2',3'-di-O-isopropylidene (1.64 g, 3.4 mmol) in ethanol (stirred under $N_2$ at 0°. After four hours the reaction mixture was poured onto a cold $Na_2CO_3$ solution (1 M, 50 mL, with gas evolution!), and was extracted with $CHCl_3$ (2×50 mL). The combined organic extracts were washed with saturated $Na_2CO_3$ solution (50 mL), dried ($MgSO_4$), and the solvent was removed under reduced pressure to give a yellow solid foam. This was purified by chromatography on silica eluting with 5% $CH_3OH$ in $CHCl_3$ to give after removal of the solvent under reduced pressure, the desired bromoadenosine (0.68 g, 45%) as an offwhite solid foam; mp 65–81° . Found C, 41.59; H, 4.54; N, 15.88; Br, 18.06; Cl, 4.84%. Calculated for $C_{15}H_{20}BrN_5N_5O_3 \cdot H_2O \cdot 0.2CHCl_3$ C, 41.45; H, 5.00; N, 15.91; Br, 18.18; Cl, 5.05%.

5'-Deoxy-5'-methylthio-N,6-cyclopentyladenosine2',3'-di-O-isopropylidene.

A solution of sodium methiolate (0.35 g, 5 mmol) and 5'-deoxy-5'-bromo-N,6-cyclopentyladenosine-2',3'-di-O-isopropylidene (1.78 g, =3.6 mmol) in DMSO (10 mL) was stirred under N₂ at 25° for 90 minutes. The reaction mixture was poured onto dilute NaOH solution (0.2N, 50 mL), and was extracted with ethyl acetate (3×25 mL). The combined extracts were washed with water (2×25 mL) and saturated brine (25 mL), and then dried (MgSO₄), and the solvent was removed under reduced pressure to give the desired thioether (1.51 g, 90%) as a brown gum containing 65 mol% ethyl acetate. Nmr (CDCl₃) 5 8.26, 7.77 (1H and 1H, 2s), 5.98 (1H, d, J=2.5 Hz), 5.77 (1H, brd, J=7 Hz), 5.46 (1H, d of d, J=2.5, 6.5 Hz), 4.98 (1H, d of d, J=6.5, 3 Hz), 4.4–4.7 (1H, m), 4.31 (1H, d of t $J_d$=3 Hz, $J_t$=7 Hz), 2.74, 2.68 (2H, ABq of ds $J_{AB}$= 13.5 Hz, $J_d$=7 Hz), 1.95–2.15 (2H, m), 2.05 (3H, s), 1.3–1.7 (6H, m), 1.58, 1.37 (3H +3H, 2s).

5'-Deoxy-5'-methylthio-N,6-cyclopentyladenosine.

Trifluoroacetic acid (9 mL) containing water (1 mL) at 0° was added to a solution of 5'-deoxy-5'-methylthio-N,6-cyclopentyladenosine2',3'-di-O -isopropylidene (1.51 g, =3.2 mmol) in ethanol (3 mL) stirred under N₂ at 0°. After two hours the reaction mixture was poured onto aqueous Na₂CO₃ solution (1M, 100 mL, with gas evolution!) The combined extracts were washed with water (2×25 mL), and saturated brine (25 mL), then dried (MgSO₄), and the solvent removed under reduced pressure. The residual gum was chromatographed on silica eluting with 5% methanol in CHCl₃ to give the desired adenosine (0.87 g, 74%) as a tan colored solid foam; mp 50–60°. Calculated for $C_{16}H_{23}N_5O_3S.0.2CHCl_3$ C, 49.97; H, 5.96; N, 17.99%. Found C, 49.82; H, 5.95; N, 17.99%.

5'-Deoxy-N,6-cyclopentyladenosine-2',3'-di-O-isopropylidene.

5'-Deoxy-5'-bromo-N,6-cyclopentyladenosine2',3'-di-O -isopropylidene (0.77 g, =1.7 mmol) was hydrogenated in methanol (100 mL) containing triethylamine (0.3 mL) and Pd/C (20%, 0.2 g) at 50 psi for 26 hours at 25°. The catalyst was removed by filtration, the solvent was removed under reduced pressure, and the residual gum was added to water (25 mL) and extracted with ethyl acetate (2×25 mL). The combined extracts were washed with water (25 mL), and saturated brine (25 mL) and then dried (MgSO₄) give the desired isopropylidene (0.41 g, 65%) as a yellow-brown gum. Nmr (d₆ DMSO) 5 8.25, 8.17 (1H and 1H, 2s), 7.55 (1H brs), 6.03 (1H, d J=2.5 Hz), 545 (1H, d of d, J=2.5, 6 Hz) 4.74 (1H, d of d J=6, 3 Hz), 4.19 (1H, d of q $J_d$=3 Hz $J_q$=7 Hz), 1.4–2.1 (8H, m), 1.53 (3H, s), 1.32 (3H, s), 1.25 (3H, d, J=7 Hz).

5'-Deoxy-N,6-cyclopentyladenosine

A solution of 5'-deoxy-N,6-cyclopentyladenosine2',3'-di-O -isopropylidene in 50% aqueous formic acid (5 mL) was heated under N₂ at 50° for four hours. The solvent was removed under reduced pressure and the residual oil was dissolved in ethyl acetate (25 mL) and washed with saturated NaHCO₃ solution (10 mL), and saturated brine (10 mL) and then dried (MgSO₄). The solvent was removed under reduced pressure, and the residual solid foam was purified by preparative tlc eluting with 2% CH₃OH in ethyl acetate. The major band (rf 0.31) was extracted with CH₂Cl₂/CH₃OH, and the solvent removed under reduced pressure to give the desired nucleoside (0.10 g, 32%) as a light yellow gum. Nmr (d₆ DMSO) 5 8.34, 8.23 (1H and 1H, 2s), 7.72 (1H, br d J=8 Hz), 5.87 (1H, d, J=5 Hz), 5.45 (1H, d, J=6 Hz), 5.18 (1H, d J=5.4 Hz), 4.67 (1H, q, J=5 Hz), 4.45–4.7 (1H, brs), 3.95–4.10 m), 1.31 (3H, d).

I claim:

1. A process for the preparation of a compound of the formula (I)

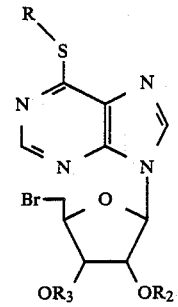

wherein
R is alkyl of from one to six carbons, aryl, heteroaryl or aralkyl,
R² and R³ are independently hydrogen, alkyl of from one to six carbons, alkanoyl of from two to six carbons, benzoyl, and R² and R³ are taken together to form alkylidene of from one to six carbons;
which comprises treating a compound of the formula (II)

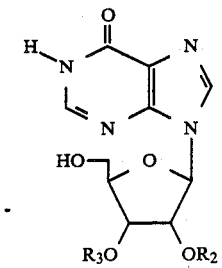

wherein R₂ and R₃ are as defined above with the proviso that R₂ and R₃ are not hydrogen
with Ar₃PBr₂ or (ArO)₃PBr₂ wherein Ar is aryl in a solution and then RSH wherein R is as defined above;
and optionally deprotecting to obtain the compound of formula I defined above.

2. A process of claim 1 wherein R is phenyl and Ar is phenyl and R₂ and R₃ are taken together and are isopropylidene.

3. A process of claim 1 wherein the solvent is pyridine.

4. A process for the preparation of a compound of the formula (V)

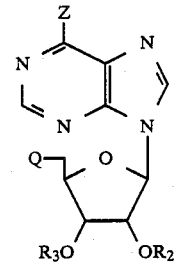

wherein Z is RS(O)$_q$ wherein R is alkyl of from one to six carbons, aryl, heteroaryl, aralkyl; and q is an integer of zero or two, or NR$_7$R$_8$ wherein R$_7$ and R$_8$ are independently hydrogen, alkyl of from one to six carbons, cycloalkyl having three to eleven membered ring, aryl, aralkyl, bicyclo [2.2.1]or [2.2.2.]heptyl unsubstituted or substituted by from one to five methyl groups, 1- or 2- naphthyl, or a group selected from

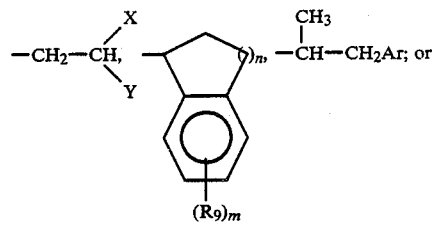

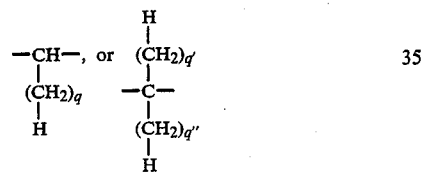

wherein X and Y are independently aryl or heteroaryl, n is one, two or three, m is one or two, A is a bond, O, S,

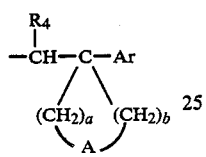

wherien q, q' or q'' are independently an integer of one to four, inclusive;

a and b are independently an integer of from zero to three, inclusive, with the proviso that if A is a bond then the sum of a and b must be at leat two and A is other than a bond then the sum of a and b must be at least one;

R$_4$ is hydrogen or alkyl of from one to six carbons with the proviso that if R$_7$ and R$_8$ are the same then both must be hydrogen or alkyl of from one to six carbons; and Q is hydrogen, halogen, cyano, azido, amino, lowr alkoxy, lower acyloxy, lower thioalkyl, hydrazino, hydroxylamino, phosphino, dialkyl or diarylcuprato which comprises
(1) preparing a compound of the formula I by the process of claim 1; and (2) treating the compound of the step (1) with an oxidizing agent to obtain a compound of the formula (XXX)

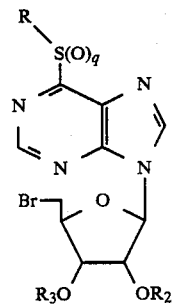

wherein R, R$_2$ and R$_3$ are as defined above;
(3) treating the compound of the formula XXX with a compound of the formula HNR$_7$R$_8$ wherein R$_7$ and R$_8$ are as defined above to obtain a compound of the formula (IV)

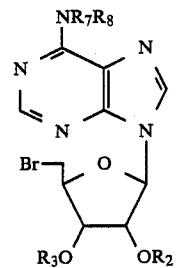

or
(4) treating the compound of the formula XXX or the compound of the formula IV
with a nucleophile selected from the group consisting of hydrogen, halogen, cyano, azido, amino, lower alkoxy, lower acyloxy, lower thioalkyl, hydrazino, hydroxylamino, phosphino, dialkyl or diarylcuprato
in an aprotic solvent to obtain the compound V.

5. A process of claim 4 wherein the compound V is further hydrolyzed to produce the compound of the formula

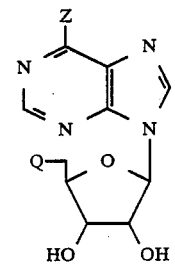

* * * * *